US012564606B2

(12) United States Patent
Lee et al.

(10) Patent No.: US 12,564,606 B2
(45) Date of Patent: Mar. 3, 2026

(54) PHARMACEUTICAL COMPOSITION FOR TREATING WOUNDS

(71) Applicants: Medicosbiotech, Inc, Seoul (KR); Korea Advanced Institute of Science and Technology, Daejeon (KR)

(72) Inventors: Sang Yup Lee, Daejeon (KR); Won Min Yoo, Seoul (KR); Sooncheol Kim, Seoul (KR); Hannah Chung, Daejeon (KR); Jiyong Kim, Daejeon (KR)

(73) Assignees: MEDICOSBIOTECH, INC, Seoul (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 849 days.

(21) Appl. No.: 17/296,301

(22) PCT Filed: Nov. 21, 2019

(86) PCT No.: PCT/KR2019/016011
§ 371 (c)(1),
(2) Date: May 24, 2021

(87) PCT Pub. No.: WO2020/106074
PCT Pub. Date: May 28, 2020

(65) Prior Publication Data
US 2022/0008463 A1 Jan. 13, 2022

(30) Foreign Application Priority Data
Nov. 23, 2018 (KR) ........................ 10-2018-0146287

(51) Int. Cl.
*A61K 35/16* (2015.01)
*A61K 9/19* (2006.01)
*A61K 38/17* (2006.01)
*A61P 17/02* (2006.01)

(52) U.S. Cl.
CPC ............... *A61K 35/16* (2013.01); *A61K 9/19* (2013.01); *A61K 38/1767* (2013.01); *A61P 17/02* (2018.01)

(58) Field of Classification Search
None
See application file for complete search history.

(56) References Cited
U.S. PATENT DOCUMENTS

| | | | |
|---|---|---|---|
| 5,183,805 A | 2/1993 | Lee et al. | |
| 5,264,207 A | 11/1993 | Bommelaer et al. | |
| 5,897,880 A | 4/1999 | Drizen et al. | |
| 5,981,606 A | 11/1999 | Martin et al. | |
| 6,165,978 A | 12/2000 | Rodgers et al. | |
| 8,017,157 B2 | 9/2011 | Yoo et al. | |
| 2012/0231499 A1* | 9/2012 | Lee ................. | C07K 14/43518 264/178 F |

| | | | |
|---|---|---|---|
| 2013/0017299 A1 | 1/2013 | Doby et al. | |
| 2013/0172999 A1 | 7/2013 | Kaplan et al. | |
| 2016/0023588 A1 | 1/2016 | Peterson | |
| 2016/0235889 A1* | 8/2016 | Pallotta .................... | A61K 8/66 |
| 2017/0035475 A1 | 2/2017 | Thoren et al. | |
| 2017/0354754 A1 | 12/2017 | Liden | |

FOREIGN PATENT DOCUMENTS

| | | |
|---|---|---|
| CA | 2045144 A1 | 7/1990 |
| EP | 0575484 B1 | 9/2000 |
| JP | 05070365 A2 | 12/1991 |
| KR | 100315168 B1 | 11/2001 |
| KR | 16503020 | 5/2003 |
| KR | 100518152 B1 | 9/2005 |
| KR | 1020070113876 A | 11/2007 |
| KR | 101317420 B1 | 10/2013 |
| KR | 1020130145977 A | 11/2013 |
| KR | 20150061806 A | 6/2015 |
| KR | 101617075 B1 | 4/2016 |
| WO | 9413333 A1 | 6/1994 |
| WO | 9613164 A1 | 5/1996 |
| WO | 9630038 A1 | 10/1996 |
| WO | 200024378 A1 | 5/2000 |
| WO | WO03094937 A1 | 11/2003 |
| WO | 2007139291 A1 | 12/2007 |
| WO | 11112046 A2 | 9/2011 |

OTHER PUBLICATIONS

Ersel (Medical Science Monitor (2016), vol. 22, pp. 1064-1078).*
Office Action issued on Apr. 1, 2024 for Chinese Patent Application 201980083434.3.
English Translation of Office Action issued on Apr. 1, 2024 for Chinese Patent Application 201980083434.3.
Search Report issued on Mar. 29, 2024 for Chinese Patent Application 201980083434.3.
Bari, E., et a., "Association of silk sericin and platelet lysate: Premises for the formulation of wound healing active medications", International Journal of Biological Macromolecules, 2018, pp. 37-47, vol. 119, Publisher: Elsevier.
Xu, N., et al., "Wound healing effects of a Curcuma zedoaria plysaccharide with platelet-rich plasma exosomes assembled on chitosan/silk hydrogel sponge in a diabetic rat model", International Journal of Biological Macromlecules, 2018, pp. 102-107, vol. 117, Publisher: Elsevier.
Office Action issued on Aug. 22, 2022 in counterpart Japanese Patent Application No. 2021-529098, Aug. 22, 2022.
English Translation of Office Action issued on Aug. 22, 2022 in counterpart Japanese Patent Application No. 2021-529098, Aug. 22, 2022.

(Continued)

*Primary Examiner* — Susan Hoffman
(74) *Attorney, Agent, or Firm* — HULTQUIST, PLLC; Steven J. Hultquist

(57) ABSTRACT

The present invention relates to a pharmaceutical composition for treating wounds, containing a silk protein and a plasma component as active ingredients. According to the present invention, wounds can be more effectively healed by using synergistic effects of a silk protein and a plasma component.

8 Claims, 2 Drawing Sheets
Specification includes a Sequence Listing.

(56)                    References Cited

OTHER PUBLICATIONS

Xu, N., et al., "Wound healing effects of a Curcuma zedoaria polysaccharide with platelet-rich plasma exosomes assembled on chitosan/silk hydrogel sponge in a diabetic rat model", International Journal of Biological Macromlecules, 2018, pp. 102-107, vol. 117, Publisher: Elsevier.
Nishida et al., 1983 "Fibronectin—A New Therapy for Corneal Trophic Ulcer," Arch Ophthalmol 101(7):1046-48.
Wysocki et al., 1988 "Topical Fibronectin Therapy for Treatment of a Patient With Chronic Stasis Ulcers," Arch Dermatol 124(2):175-77.

International Search Report of the International Searching Authority for Application No. PCT/KR2019/016011, mailed Feb. 25, 2020 (4 pages).
Written Opinion of the International Searching Authority for Application No. PCT/KR2019/016011, mailed Feb. 25, 2020 (8 pages).
International Preliminary Report on Patentability of the International Searching Authority for Application No. PCT/KR2019/016011, mailed May 25, 2021 (5 pages).
International Search Report from related International Application No. PCT/KR2019/016011, mailed Feb. 25, 2020 (4 pages).
Written Opinion from related International Application No. PCT/KR2019/016011, mailed Feb. 25, 2020 (4 pages).

* cited by examiner

PHARMACEUTICAL COMPOSITION FOR TREATING WOUNDS

1. SEQUENCE LISTING

The application contains a Sequence Listing with has been submitted in ASCII format via EFS and is hereby incorporated by reference. The ASCII copy, created on May 7, 2021, is named PF_B2554_ST25.txt and is 1,211 bytes in size.

2. TECHNICAL FIELD

The present invention relates to a pharmaceutical composition for treating wounds, and more specifically, to a pharmaceutical composition for treating wounds comprising a silk protein and a blood plasma or serum component.

3. BACKGROUND

Substances for treating skin wounds that have been known to date include growth factors such as epidermal growth factors (EGFs), acid and basic fibroblast growth factors (acid and basic FGFs), transforming growth factors (TGF-$\alpha$ and TGF-$\beta$) and insulin-like growth factors (IGF-I and II), adhesion factors such as fibronectin, laminin and vitronectin, retinoid and retinoid-like compounds, and the like.

Cytokines have been identified as growth factors relating to wound treatment, and representative examples thereof include basic fibrogrowth factors, which are produced in keratinocytes and fibroblasts and promote the growth of epithelial cells, platelet-derived growth factors (PDGFs), which are produced in platelet endothelial tissue and promote proliferation of epithelial cells along with epidermal growth factors (EGFs), transforming growth factor-$\beta$ (TGF-$\beta$), which is produced in fibroblasts and platelets and promotes the formation of connective tissue, epithelial growth factors, which are produced from the salivary glands and promote the proliferation of epithelial cells, fibroblast growth factor (FGF), and interleukin-1, which is produced in macrophages and epithelial cells and promotes growth and motility of epithelial cells. Becaplermin, which has been commercially available as a therapeutic agent for wounds for topical administration by Johnson & Johnson under the trade name of "Regranex", is a genetically engineered PDGF. EP Patent No. 0575484 discloses a pharmaceutical composition comprising PDGF and dexamethasone for regenerating and repairing mammalian tissues. U.S. Pat. No. 5,981,606 discloses a pharmaceutical composition comprising TGF-$\beta$ for wound healing. WO 96/30038 discloses a pharmaceutical composition for wound healing comprising TGF-$\beta$ fibric acid and an antioxidant. U.S. Pat. No. 5,183,805 discloses a pharmaceutical composition comprising EGF and thus having an effect of regenerating tissues. JP Patent No. 05070365 and U.S. Pat. No. 6,165,978 disclose a therapeutic agent for wounds comprising FGF.

Formulations utilizing hyaluronic acid as an active ingredient have also been reported to be useful for the treatment of skin wounds (U.S. Pat. No. 5,897,880). Formulations containing sodium hyaluronate are marketed under the trade name of IPN Wound Gel™ by LAM Pharmaceutics.

Topically applied fibronectin (glycoprotein found in blood plasma) has also been reported to be useful for increasing the healing rate in corneal wounds (Nishida, Larch Ophthalmology 101:1046 (1983)) and leg wounds (Wysocki et al. Arch. Dermatol. 124:175, 1988).

In addition, blood plasma was found to normalize abnormal cells and various cell-active substances at the wound site and to thereby exhibit a wound healing effect, and a therapeutic agent for wounds containing the same has been developed based thereon (Korean Patent No. 0518152 and Korean Patent Publication No. 2007-0113876).

Blood plasma is a pale yellow liquid from which tangible components in the blood of mammals, i.e. cells and cell fragments are isolated. When an anticoagulant is added to blood and then the mixture is centrifuged, sedimented, or is allowed to stand at a low temperature (about 0° C.), blood plasma as the upper layer and tangible components as the lower layer are separated from each other. In this case, the proportion occupied by blood plasma is about 55% although this varies slightly between men and women. Blood plasma consists of about 90% water, 7 to 8% plasma proteins, and the balance of other lipids, sugars, inorganic salts and non-proteinaceous nitrogen compounds such as urea, amino acids and uric acid. Plasma proteins are mostly produced in the liver, contain albumin and globulin as main ingredients, and further contain fibrinogen, which is related to blood coagulation. Lipids include cholesterol, lecithin and the like. Inorganic salts contain sodium, chlorine, potassium, calcium, magnesium and the like, the composition thereof is similar to that of seawater and they play a key role in maintaining normal osmotic pressure in the body. In addition, the total amount and composition of blood plasma vary greatly depending on the disease and thus are used to diagnose a disease or to detect the state of a disease.

Blood plasma is utilized in limitless applications due to the various active ingredients as described above. In particular, blood plasma contains active substances with high medical applicability such as albumin and fibrinogen, and is widely used as a source of these substances. However, blood plasma has a disadvantage of low economical efficiency because it should be separated from the blood of livestock and humans.

Meanwhile, sericin, which is a type of silk protein, is also known as silk glue, and cocoon fibers have a structure in which two strands of fibroin are covered with three layers of sericin. It was isolated from cocoon fibers by E Kramer in 1865 and named "sericin" after the Latin word "sercum" and Greek "serikon", each of which means silk. Raw threads are rough and hard due to the sericin attached thereto. The sericin is melted away in the refining process, resulting in soft texture specific to silk threads. Sericin has a remarkably high content of about 37 mol % of serine among the total amino acids thereof, and dissolves in hot water and gels when cooled.

Among silk proteins, spider silk proteins include dragline proteins and/or flagelliform proteins. The dragline silk is used by orb-weaving spiders to erect frames and radials with the nets thereof, and is lifeline that enables spiders to continuously move backwards. For this purpose, high tensile strength and elasticity are required. The combination of such properties results in higher tensile strength than other known materials. Dragline silk generally consists of two major proteins, and the primary structures of these proteins share a common repetitive architecture. The spiral capture of the orb web that is partly composed of a viscous silk, called "flagelliform silk", formed by a flagelliform gland, is elastic and can be stretched to three times its original length before breaking, but has the half the tensile strength of dragline silk. Variations in a single repeating unit may contain up to 60 amino acids and are repeated several times to form the largest portion of the spider silk sequence. These repeating units contain a limited set of distinct amino acid motifs. One motif found in all dragline silk repeating units is typically a block of 6 to 9 alanine residues. In silk threads, several polyalanine motifs form crystalline (3-sheet stacks that impart tensile strength thereto.

Silk protein is mainly used as a covering material to block a wound from the outside. A method of producing a gel-like silk protein and using the same as a wound covering material (Korea Patent No. 1,617,075) and a method of producing a silk protein in the form of a layer (film) and using the same as a wound covering material (Korean Patent No. 0,315,168) are known. However, an effect of directly treating wounds has not been known to date.

In the present invention, as a result of extensive efforts to develop more economical and effective therapeutic agents for wounds, a therapeutic agent for wounds comprising a blood plasma component and silk protein was produced, and the therapeutic agent was found to exhibit an excellent wound repair effect when applied to a wound. Based on this finding, the present invention has been completed.

4. SUMMARY

It is one object of the present invention to provide an economical and effective pharmaceutical composition for treating a wound.

It is another object of the present invention to provide a method for treating a wound comprising administering a blood plasma or serum component and a silk protein to a subject.

It is another object of the present invention to provide the use of a blood plasma or serum component and a silk protein for the treatment of a wound.

It is another object of the present invention to provide the use of a blood plasma or serum component and a silk protein for the preparation of a therapeutic agent for wounds.

To achieve the above object, the present invention provides a pharmaceutical composition for treating a wound comprising a blood plasma or serum component and a silk protein as active ingredients.

The present invention also provides a method for treating a wound comprising administering a blood plasma or serum component and a silk protein to a subject.

The present invention also provides the use of a blood plasma or serum component and a silk protein for the treatment of a wound.

The present invention also provides the use of a blood plasma or serum component and a silk protein for the preparation of a therapeutic agent for wounds.

5. BRIEF DESCRIPTION OF THE DRAWINGS

4

6. DETAILED DESCRIPTION

Figure 1:
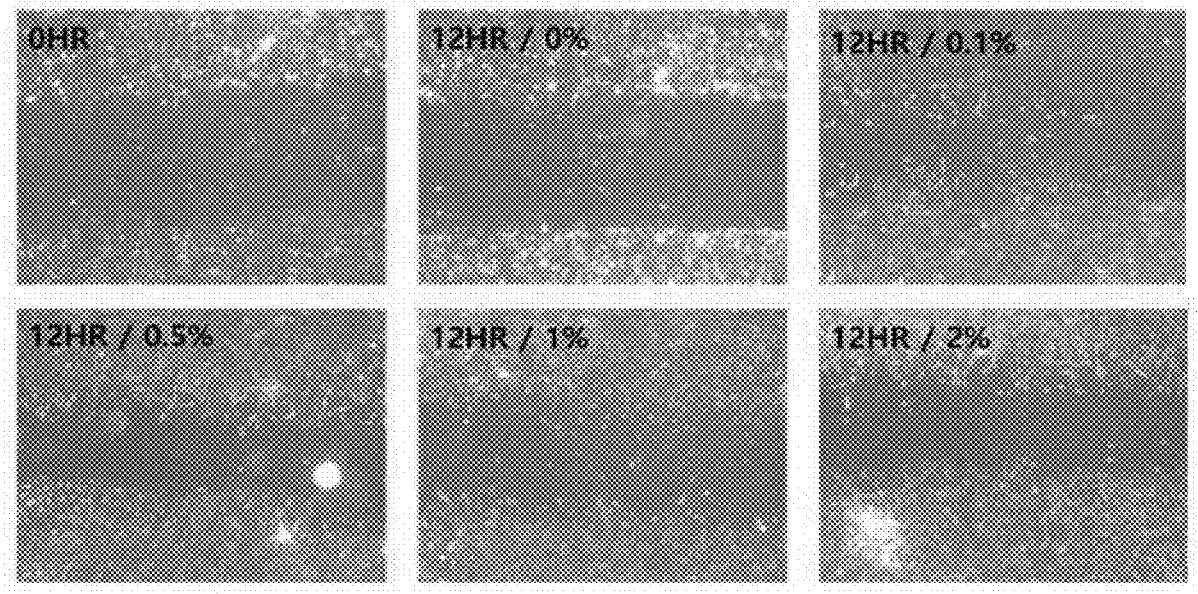
FIG. 1 shows the results of detection of the therapeutic effect of blood plasma components on a scratch wound formed on NIH3T3 cells, which are mouse fibroblasts.

Unless defined otherwise, all technical and scientific terms used herein have the same meanings as appreciated by those skilled in the field to which the present invention pertains. In general, the nomenclature used herein is well-known in the art and is ordinarily used.

In the present invention, it was found that, when a composition comprising a blood plasma or serum component and a silk protein is applied to a wound site, a better wound repair effect is obtained than when a blood plasma component or silk protein is applied thereto.

Accordingly, in one aspect, the present invention is directed to a pharmaceutical composition for treating a wound comprising a blood plasma or serum component and a silk protein as active ingredients.

In the present invention, the pH of the composition may be 3.5 to 6.5, and the blood plasma or serum may be derived from humans or livestock.

In the present invention, the blood plasma component may be obtained by separating albumin, fibrinogen and thrombin, and may be obtained by further removing at least one selected from the group consisting of heparin, anti-thrombin III, blood coagulation factor 2, blood coagulation factor 8, blood coagulation factor 9, and IgG.

In the present invention, the blood plasma or serum component may be a lyophilized formulation, and the blood plasma or serum component may be present in an amount of 0.001 to 99.999% in the composition.

In the present invention, the silk protein may be present in an amount of 0.001% to 99.999% in the composition.

In the present invention, the composition preferably comprises 0.01 to 10% of the blood plasma component and 0.001 to 10% of the silk protein, more preferably 0.1 to 2% of the blood plasma component and 0.01 to 1% of the silk protein, and even more preferably 0.2 to 1% of the blood plasma component and 0.02 to 0.1% of the silk protein.

When the composition contains the blood plasma in an amount of 10% or more, an improvement of the wound treatment effect cannot be expected in proportion to the amount of the blood plasma that is added, and when the composition contains the plasma in an amount of less than 0.01%, the wound treatment effect cannot be expected. When the composition contains the silk protein in an amount of 10% or more, an improvement of the wound treatment effect cannot be expected in proportion to the amount of the silk protein that is added, and when the composition contains the silk protein in an amount of less than 0.001%, the wound treatment effect cannot be expected.

In the present invention, the silk protein may be naturally derived or may be a recombinant silk protein, and the silk protein may be a repeating peptide unit constituting a protein selected from the group consisting of dragline silk, elastin, silk fibroin, byssus, sericin, flagelliform silk, and collagen.

In the present invention, the silk protein may have a structure in which a silk repeating peptide unit having a glycine or serine content of 1% or more is repeated 1 to 160 times.

In the present invention, the silk protein may have a molecular weight of 5 to 300 kDa.

In the present invention, the recombinant silk protein may be a recombinant spider protein.

In the present invention, the recombinant spider silk protein may be prepared by the method disclosed in Korean Patent No. 10-1317420, and may have a high molecular weight and a structure in which a peptide having the following sequence of SEQ ID NO: 1 or SEQ ID NO: 2 is repeated 1 to 96 times.

```
                                      SED ID NO 1
NH2-SGRGGLGGQGAGMAAAAAMGGAGQGGYGGLGSQGT-COOH

SED ID NO 2
NH2-SSTGSSSNTDSNSNSVGSSTSGGSSTYGYSSNSRDGSV-COOH
```

In the present invention, the wound is selected from the group consisting of non-healing traumatic wounds, destruction of tissue by irradiation, abrasion, bone gangrene, lacerations, avulsions, penetrated wounds, gunshot wounds, cuts, burns, frostbite, skin ulcers, dry skin, skin keratosis, cracks, ruptures, dermatitis, pain due to dermatophytes, surgical or vascular disease wounds, contusions, corneal wounds, pressure sores, decubitus, conditions related to poor circulation and diabetes such as diabetic skin erosion, chronic ulcers, sutures after plastic surgery, spinal injury wounds, gynecological wounds, chemical wounds and acne.

In the present invention, the formulation of the therapeutic composition may be selected from the group consisting of creams, ointments, gels, solutions, powders and patches.

In another aspect, the present invention is directed to a method for treating a wound comprising administering a blood plasma or serum component and a silk protein to a subject.

In another aspect, the present invention is directed to the use of the blood plasma or serum component and silk protein for the treatment of a wound.

In another aspect, the present invention is directed to the use of the blood plasma or serum component and silk protein for the preparation of a therapeutic agent for wounds.

As used herein, the term "wound" refers to the state in which a body is damaged, and encompasses a pathological condition in which tissue that form an internal or external surface of a body, such as skin, muscle, nerve tissue, bone, soft tissue, internal organs, or vascular tissue, is cracked or disrupted.

Examples of the wound include, but are not limited to, non-healing traumatic wounds, destruction of tissue by irradiation, abrasion, bone gangrene, laceration, avulsions, penetrated wounds, gunshot wounds, cuts, burns, frostbite, contusions (bruises), skin ulcers, dry skin, skin keratosis, cracks, ruptures, dermatitis, pain due to dermatophytes, surgical wounds, vascular disease wounds, corneal wounds, pressure sores, decubitus, conditions related to poor circulation and diabetes such as diabetic skin erosion, chronic ulcers, sutures after plastic surgery, spinal injury wounds, gynecological wounds, chemical wounds and acne, and encompass damage in any site of a subject. In this respect, the formulation according to the present invention may be very useful for repairing, replacing, ameliorating, accelerating, promoting, or healing such damaged tissues.

The blood plasma used in the present invention comprises blood plasma isolated from the blood of any species of mammal including humans, for example, the blood of livestock including sheep, goats, pigs, horses, dogs, cattle, other primates, and rodents. In the present invention, blood plasma may be easily separated from the blood by well-known conventional methods, such as centrifugation, sedimentation (precipitation) or filtration. The centrifugation may be carried out under conditions suitable for sedimentation of blood cells from blood plasma. For example, the blood is centrifuged at about 1,400 g for about 10 minutes, which is sufficient to precipitate blood cells and leukocytes, as well as virtually all cell fragments including platelets. The supernatant containing blood plasma may be easily separated from sedimented cells by standard techniques.

The filtration may be performed by passing the blood through a filter suitable for separating blood cells from plasma, and the filter is preferably a microporous membrane that enables proteins to easily penetrate therein. Methods of preserving blood plasma in various states before use, in addition to a fresh liquid plasma or liquid formulation obtained by centrifugation or sedimentation after blood collection, are known. Examples of such formulations include fresh frozen formulations, freeze-precipitated formulations, lyophilized formulations, concentrated formulations and the like. In the present invention, any type of blood plasma described above may be used.

The composition according to the present invention may be applied directly to the wound as a liquid or powder, that is, may be spread over the wound. When the composition is provided as a sheet, the wound area to which the composition is applied may be suitably dressed to protect the wound and prevent a decrease in the therapeutic effect of the active ingredient. The dressing may be any commercially available or commonly known dressing. Examples of the commercially available dressing include Comfeel, Duoderm, Tegaderm and Opsite.

The composition comprising a pharmaceutically effective amount of the blood plasma component as an active ingredient according to the present invention may be formulated in various forms along with a pharmaceutically acceptable carrier. The formulation may be carried out according to methods known in the art. The formulation includes, but is not limited to, conventional external formulations such as liquid coatings, sprays, lotions, creams, gels, pasta, liniment, ointments, aerosols, powders, and transdermal absorption agents. These formulations are disclosed in the document [Remington's Pharmaceutical Science, 15th Edition, 1975, Mack Publishing Company, Easton, PA. 18042 (Chapter 87: Blaug, Seymour)], which is a generally known prescription in all pharmaceutical and chemical fields.

In the external formulation of the present invention, the pharmaceutically acceptable carrier may vary depending on the formulation thereof, but may include: hydrocarbons such as Vaseline, liquid paraffin, and gelled hydrocarbons (also called plastibase); animal and vegetable oils such as medium-chain fatty acid triglycerides, pork fat, hard fat and cacao oil; higher fatty acid alcohols and esters thereof such as cetanol, stearyl alcohol, stearic acid, and isopropyl palmitate; water-soluble bases such as macrogol (polyethylene glycol), 1,3-butylene glycol, glycerol, gelatin, sucrose, and sugar alcohol; emulsifiers such as glycerin fatty acid ester, polyoxyl stearate, and polyoxyethylene hardened castor oil; adhesives such as acrylic acid ester and sodium alginate; propellants such as liquefied petroleum gas and carbon dioxide; and preservatives such as paraoxybenzoic acid esters, and the external preparation of the present invention may be prepared using the same according to a conventional method. Further, in addition thereto, stabilizers, fragrances, colorants, pH adjusters, diluents, surfactants, preservatives, antioxidants and the like may be mixed as necessary. The external formulation of the present invention may be applied to a local wound by a conventional method.

In addition, the external formulation according to the present invention may be used in the state of being adhered to a solid support such as a wound peeling cover of a conventional band-aid. The adhesion is carried out by saturating the solid support with a blood plasma fraction from which tangible (commercial) components have been removed, followed by dehydration. In an embodiment of the present invention, the solid support is first coated with an adhesive layer to improve adhesion of the plasma component, from which the tangible (commercial) components have been removed, to the solid support. Examples of the adhesive agent include polyacrylate and cyanoacrylate.

A variety of formulations of this type are commercially available, and examples thereof include a band-aid (Smith & Nephew Ltd) having a non-adhesive wound peeling cover in the form of a perforated plastic film, a BAND-AID* in the form of a thin strip, patch, spot or plastic strip from Johnson & Johnson; a Curity CURAD (Ouchless) band-aid from Colgate-Palmolive Co (Kendall); and STIK-TITE* elastic strips from American WhiteCross Laboratories, Inc.

In one embodiment, the pharmaceutical composition according to the present invention may be formulated in the form of a liquid coating agent by mixing a blood plasma powder with physiological saline at a predetermined volume ratio and adjusting the pH to 3.5 to 6.5. In another embodiment, the pharmaceutical composition according to the present invention may be formulated in the form of an ointment by mixing the blood plasma powder of the present invention with a water-soluble ointment base and then adding physiological saline thereto. In a preferred embodiment, the pharmaceutical composition according to the present invention may be formulated by adjusting the pH of the ointment to 3.5 to 6.5.

Pharmaceutical carriers such as gels or microspheres may be used to accelerate wound healing in the present invention. U.S. Pat. No. 5,264,207, WO 2000/24378, WO 96/13164 and WO 94/13333 disclose one or more microspheres of polymers that act as carriers for active pharmaceutical or cosmetic substances.

The pharmaceutical composition of the present invention may be used to treat various wound symptoms in mammals. The pharmaceutical composition is effective in the treatment of infection, malignancy, lack (constriction) of large vascular artery, lack of small vascular artery, blockage or lack of deep vein, lack of superficial vein, lymphatic disorder, endogenous poor circulation, blood abnormalities, collagen vascular abnormalities, radiation dermatitis, and most malignant ulcers due to nutritional causes and the like.

The pharmaceutically effective amount of the blood plasma component used in the composition of the present invention refers to an amount of the active ingredient exhibiting a therapeutic effect on wounds by normalizing abnormal cells and various cellular active substances in the wound sites. The effective amount may vary depending on the wound type of the patient, the application site, the number of applications, the application time, the formulation, the condition of the patient, the type of adjuvant, and the like. The number of administrations may be twice a day to once a week. In one embodiment, the effective daily amount of the pharmaceutical composition of the present invention is 0.01 to 0.1 g/cm$^2$, preferably 0.02 to 0.09 g/cm$^2$, and more preferably 0.02 to 0.07 g/cm$^2$, when the powder is applied to a wound from which all skin has been lost.

Hereinafter, the present invention will be described in more detail with reference to examples. However, it will be obvious to those skilled in the art that these examples are provided only for illustration of the present invention and should not be construed as limiting the scope of the present invention.

7. EXAMPLES

Example 1: Preparation of Plasma Fraction

Fresh blood (The Korean Society for Blood Transfusion) derived from a patient who was determined to be negative for possible pathogens including HIV, HCV and HBV was thawed in a water bath at 30° C. and then centrifuged at 3,000 rpm for 10 minutes and pale yellow plasma as the upper layer, excluding precipitates such as red blood cells and white blood cells, was separated.

The separated plasma was collected in a glass tube to which an anticoagulant such as EDTA or heparin was not added, the plasma was allowed to stand overnight at 4° C., and the precipitated fibrinogen clot was removed using a Pasteur pipette. The blood from which the clot was removed was centrifuged at 4° C. and 4,000 rpm for 20 minutes to obtain a plasma fraction from which fibrinogen was removed.

Thrombin present in the fibrinogen-free plasma fraction was separated under acidic conditions. In order to precipitate prothrombin present in the plasma fraction from which fibrinogen was removed, the pH of the plasma fraction was lowered to 5.1 to 5.3 using an acetic acid solution. The solution with lowered pH was allowed to stand at 20° C. for 1 hour to completely precipitate prothrombin, followed by centrifugation at 20° C. and 4,200 rpm for 20 minutes to remove the precipitated thrombin, and a plasma fraction from which fibrinogen and thrombin were removed was obtained.

Albumin contained in the fibrinogen- and thrombin-free plasma fraction was removed using a SwellGel Blue albumin removal kit (Pierce Biotechnology, USA) according to the manufacturer's method. Through the above albumin removal method, a plasma fraction from which the commercial component was removed was obtained.

Example 2: Virus Inactivation of Plasma Fraction

The commercial component-free plasma fraction obtained in Example 1 was subjected to the following three methods in succession to inactivate viruses that may be present in the plasma component.

(1) Gamma Irradiation

Fibrinogen/thrombin/albumin-free and silk protein peptide-containing plasma fraction was irradiated with a total of 25 kGy of gamma rays at an intensity of 1.8 kGy/hr using a cobalt source ($^{60}$Co) at 15° C.

(2) Methylene Blue Light Treatment

The fibrinogen/thrombin/albumin-free and silk protein peptide-containing plasma fraction that had been irradiated with gamma rays was added with methylene blue at a final concentration of 1 μM, and was irradiated with white light at 60,000 lux for 1 hour. The remaining methylene blue was removed by filtration, frozen at −80° C. for 8 hours, dried at −48° C. for 7 days, and lyophilized.

(3) Steam Treatment

The fibrinogen/thrombin/albumin-free and silk protein peptide-containing plasma fraction was sieved, pulverized and homogenized, and then steam was slowly injected into the fraction to adjust the water content to 8% (w/w) in a stainless steel tank. The steam-treated plasma was transferred to a stainless steel cylinder filled with dry nitrogen, oxygen was removed therefrom, and then the plasma was heated at 60° C. for 10 hours to obtain a plasma fraction in which the virus was inactivated.

Example 3: Preparation of Plasma Fraction and Recombinant Spider Silk Protein The plasma fraction, in which the virus was inactivated, obtained in Example 2 was added to 1N HCl (hydrochloric acid) or 1N NaOH (sodium hydroxide), while stirring. The pH was measured with a pH meter (Orion) and adjusted to 5.5, followed by lyophilizing to obtain a plasma fraction.

The lyophilizing was performed slowly at −30 to −40° C. at 40.9 to 77.5 Torr for 12 hours using a general lyophilizer, and a 0.2 μm sterilization filter was mounted to obtain a dried plasma component, which was used to detect the wound treatment effect.

The recombinant spider silk protein was prepared using the following method.

The recombinant spider silk protein was prepared by the method described in a prior patent (Korean Patent No. 10-1317420) for producing a recombinant silk protein.

A high-molecular-weight recombinant silk or silk-like protein having a structure in which the peptide having the sequence of SEQ ID NO: 1 is repeated 48 times was used.

```
                                        SEQ ID NO: 1
NH2-SGRGGLGGQGAGMAAAAMGGAGQGGYGGLGSQGT-COOH
```

Example 4: Confirmation of Wound Healing Effect of Plasma Fraction

In order to confirm the wound healing effect of the lyophilized plasma fraction prepared in Example 3, an experiment to determine wound healing was conducted using a mouse fibroblast NIH3T3 cell line (KCTC 4612). NIH3T3 cells were seeded at a concentration of 500,000/ plate on a cell culture plate and grown to confluence in a DMEM medium (DMEM, Gibco) for cell growth supplemented with 10% fetal bovine serum (FBS, Thermo Fisher) and 1% penicillin streptomycin (Pen-strep, Sigma-Aldrich) for 1 week.

Then, the cells were starved using a serum-free medium not containing FBS for one day. Then, to determine the wound healing effect, the cells grown on the plate were scratched at regular intervals and were treated with serum-free medium supplemented with the plasma fraction at concentrations of 0.1% (w/v), 0.5%, (w/v), 1% (w/v) and 2% (w/v).

Only serum-free medium was added to perform the experiment as a negative control.

The wound healing effect of the cells was observed for 12 hours. As can be seen from FIG. 1, the growth of fibroblasts was observed in the scratch area in the experimental group to which the therapeutic agent for wounds was added, and the most effective wound healing could be obtained when 0.5% of the plasma fraction was added.

Example 5: Confirmation of Wound Healing Effect of Wound Treatment Formulation Containing Plasma Fraction and Sericin Protein In order to confirm the wound healing effect of the wound treatment formulation containing the lyophilized plasma fraction obtained in Example 3 and sericin protein (Sigma-Aldrich), an experiment to determine wound healing was conducted using the NIH3T3 cell line in the same manner as in Example 4. In the same manner as in Example 4, the cells were grown to confluence in a cell growth medium containing 10% FBS, and were then starved using a serum-free medium for a day. Then, in order to confirm the wound healing effect, the cells grown on the plate were scratched, a plasma component was added at a concentration of 0.5% to a serum-free medium, and sericin protein was added at concentrations of 0.05% (w/v) and 0.5% (w/v). Experiments were performed on, as control groups, a group treated with only serum-free medium and a group containing only a plasma component. The experimental groups were cultured for 12 hours, and then whether or not the scratched wound was treated was determined.

Figure 2:
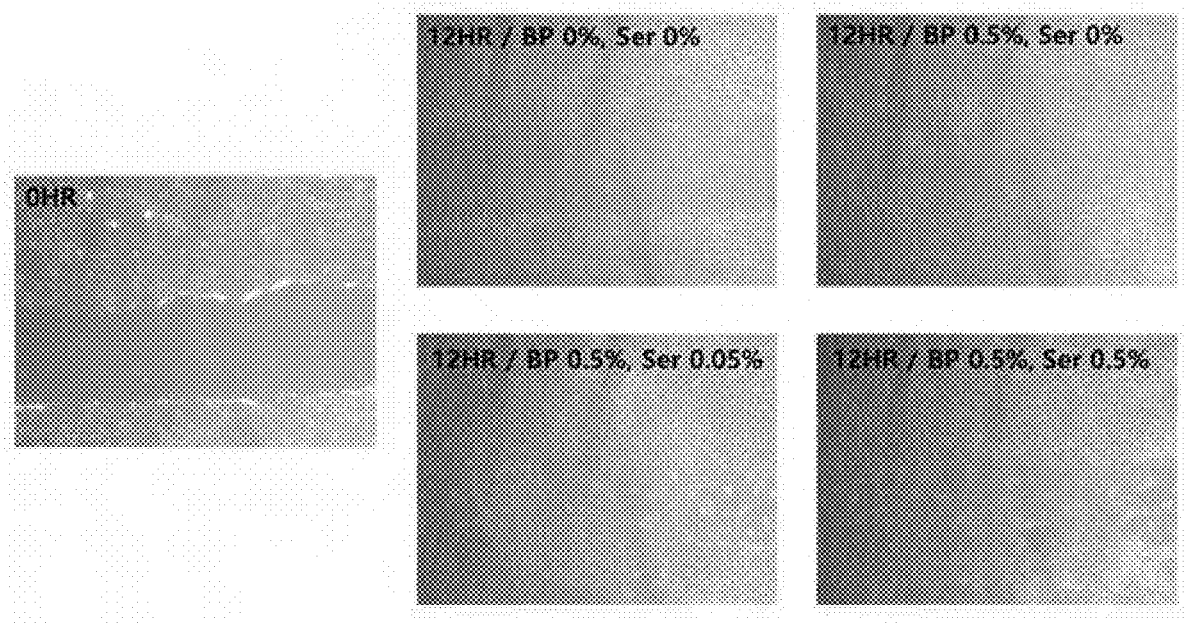
FIG. 2 shows the results of detection of the therapeutic effect of blood plasma components and sericin protein on the scratch wound formed on NIH3T3 cells, which are mouse fibroblasts.

As a result, as can be seen from FIG. 2, the group to which the plasma fraction (0.5%) and the sericin protein (0.05%) were added (BP 0.5%, Ser 0.05%) had better therapeutic effect than the group containing only the plasma component. This indicates that the optimal concentration of the sericin protein that is mixed was 0.05%.

Example 6: Confirmation of Wound Healing Effect of Component Containing Plasma Fraction and Recombinant Spider Silk Protein In order to confirm the wound healing effect of the formulation containing the lyophilized plasma fraction and the recombinant silk protein, obtained in Example 3, an experiment to determine wound healing was performed using the NIH3T3 cell line in the same manner as in Example 4.

In the same manner as in Example 4, the cells were grown to confluence in a cell growth medium containing 10% FBS and were starved using a serum-free medium for one day, and the cells grown on a plate were scratched in order to confirm the wound healing effect.

The prepared plasma component was added at a concentration of 0.5% (w/v) to a serum-free medium, and the recombinant silk protein was added thereto at concentrations of 0.05% (w/v), 0.1% (w/v), and 0.5% (w/v). Experiments were performed on, as control groups, a group treated with only serum-free medium and a group containing only a plasma component. The experimental groups were cultured for 12 hours, and then whether or not the scratched wound was treated was determined.

Figure 3:
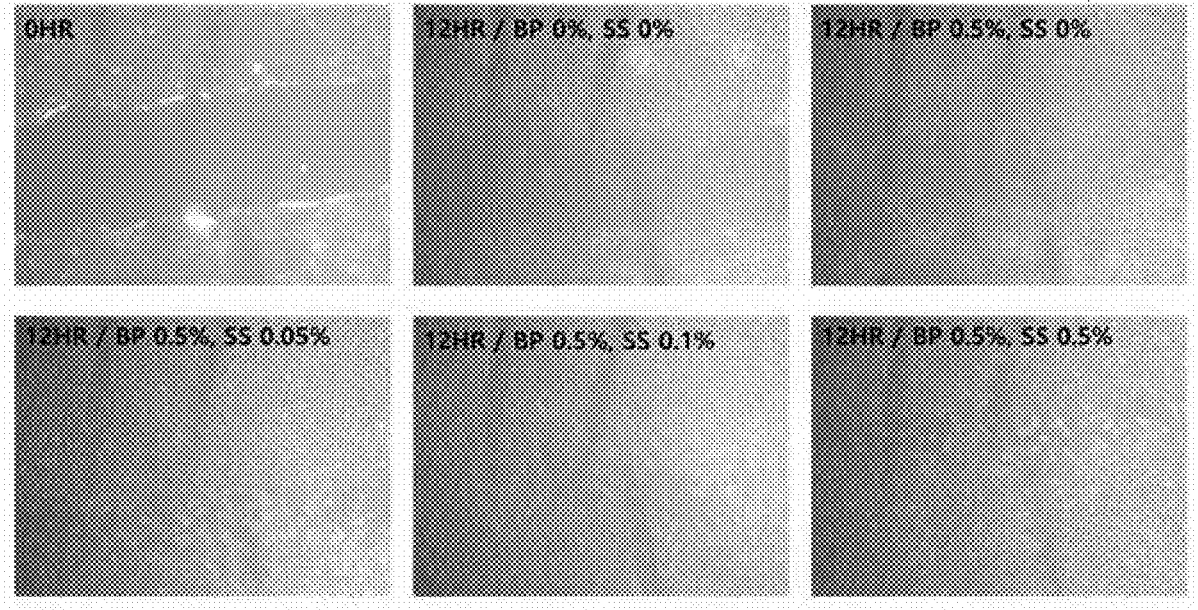
FIG. 3 shows the results of detection of the therapeutic effect of plasma components and recombinant spider silk protein on the scratch wound formed on NIH3T3 cells, which are mouse fibroblasts.

As a result, as can be seen from FIG. 3, the group to which both the plasma fraction and the recombinant spider silk protein were added was more effectively filled with new cells and thus exhibited a better therapeutic effect than the group treated only with the plasma fraction. When 0.05% of the recombinant spider silk protein was added, the best wound-healing ability was observed. This indicates that the optimal concentration of the recombinant spider silk protein mixture was 0.05%.

8. INDUSTRIAL APPLICABILITY

According to the present invention, wounds can be treated more efficiently through the synergistic effect of silk protein and plasma components.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. A method for treating a wound in a subject in need thereof, the method comprising administering to the subject a composition comprising, as active ingredients: 0.1-2% (w/v) of a blood plasma and 0.1-1% (w/v) of a dragline silk protein in which the peptide represented by SEQ ID NO: 1 is repeated 48 times.

2. The method according to claim 1, wherein the blood plasma is derived from humans or livestock.

3. The method according to claim 1, wherein the wound is selected from non-healing traumatic wounds, destruction of tissue by irradiation, abrasion, bone gangrene, lacerations, avulsions, penetrated wounds, gunshot wounds, cuts, burns, frostbite, skin ulcers, dry skin, skin keratosis, cracks, ruptures, dermatitis, pain due to dermatophytes, surgical or vascular disease wounds, contusions, corneal wounds, pressure sores, decubitus, conditions related to poor circulation, and diabetes.

4. The method according to claim 1, wherein the composition is provided as a formulation selected from creams, ointments, gels, solutions, powders, and patches.

5. The method according to claim 1, wherein the composition has a pH of 3.5 to 6.5.

6. The method according to claim 1, wherein the composition comprises a blood plasma component, and the blood plasma component is a lyophilized formulation.

7. The method according to claim 1, wherein the composition is a pharmaceutical composition further comprising a pharmaceutically acceptable carrier.

8. The method according to claim 1, wherein the wound is selected from diabetic skin erosion, chronic ulcers, sutures after plastic surgery, spinal injury wounds, gynecological wounds, chemical wounds, and acne.

*     *     *     *     *

SEQUENCE LISTING

<160> NUMBER OF SEQ ID NOS: 2

<210> SEQ ID NO 1
<211> LENGTH: 35
<212> TYPE: PRT
<213> ORGANISM: Artificial Sequence
<220> FEATURE:
<223> OTHER INFORMATION: spider silk peptide

<400> SEQUENCE: 1

Ser Gly Arg Gly Gly Leu Gly Gly Gln Gly Ala Gly Met Ala Ala Ala
1               5                   10                  15

Ala Ala Met Gly Gly Ala Gly Gln Gly Gly Tyr Gly Gly Leu Gly Ser
            20                  25                  30

Gln Gly Thr
        35

<210> SEQ ID NO 2
<211> LENGTH: 38
<212> TYPE: PRT
<213> ORGANISM: Artificial Sequence
<220> FEATURE:
<223> OTHER INFORMATION: sericin silk peptide

<400> SEQUENCE: 2

Ser Ser Thr Gly Ser Ser Ser Asn Thr Asp Ser Asn Ser Asn Ser Val
1               5                   10                  15

Gly Ser Ser Thr Ser Gly Gly Ser Ser Thr Tyr Gly Tyr Ser Ser Asn
            20                  25                  30

Ser Arg Asp Gly Ser Val
        35